United States Patent
Hutchinson

(10) Patent No.: US 10,448,876 B2
(45) Date of Patent: Oct. 22, 2019

(54) HYPERSPECTRAL IMAGING SYSTEMS AND RELATED METHODS

(75) Inventor: George Hutchinson, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 867 days.

(21) Appl. No.: 13/558,888

(22) Filed: Jul. 26, 2012

(65) Prior Publication Data

US 2013/0030269 A1    Jan. 31, 2013

Related U.S. Application Data

(60) Provisional application No. 61/511,858, filed on Jul. 26, 2011.

(51) Int. Cl.
*A61B 5/00* (2006.01)
*A61B 5/1455* (2006.01)

(52) U.S. Cl.
CPC .......... *A61B 5/4041* (2013.01); *A61B 5/1455* (2013.01); *A61B 5/4076* (2013.01); *A61B 5/441* (2013.01); *A61B 5/4542* (2013.01)

(58) Field of Classification Search
CPC ........ G01J 7/00; A61B 5/4041; A61B 5/1455; A61B 5/4542; A61B 5/441; A61B 5/4076
USPC ....................................... 600/476
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Peter Luong

(57) ABSTRACT

Systems and methods for analyzing sublingual microcirculation perfusion and identifying particular nerve tracts. In exemplary embodiments, a digital micro-mirror device is configured to direct a reflected light to a subject area and a controller is configured to alter a parameter of the reflected light.

7 Claims, 6 Drawing Sheets

(56) References Cited

U.S. PATENT DOCUMENTS

| | | | |
|---|---|---|---|
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,055,447 A * | 4/2000 | Weil | A61B 5/0261 600/309 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,639,309 B2 * | 1/2014 | Shuler | A61B 5/0215 600/323 |
| 8,666,468 B1 * | 3/2014 | Al-Ali | 600/324 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0069485 A1 * | 4/2003 | Konishi et al. | 600/317 |
| 2004/0127800 A1 * | 7/2004 | Kimball | A61B 5/0261 600/483 |
| 2004/0147808 A1 * | 7/2004 | MacAulay | G02B 21/0028 600/160 |
| 2005/0254008 A1 * | 11/2005 | Ferguson et al. | 351/205 |
| 2006/0007439 A1 * | 1/2006 | Corcoran | G01J 3/02 356/317 |
| 2006/0184037 A1 * | 8/2006 | Ince | A61B 1/042 600/476 |
| 2007/0024946 A1 * | 2/2007 | Panasyuk | A61B 5/0059 359/253 |
| 2007/0200927 A1 * | 8/2007 | Krenik | 348/47 |
| 2007/0232940 A1 * | 10/2007 | Fine | A61B 5/14535 600/504 |
| 2007/0249913 A1 * | 10/2007 | Freeman | A61B 5/0059 600/300 |
| 2009/0105605 A1 * | 4/2009 | Abreu | 600/549 |
| 2009/0118622 A1 * | 5/2009 | Durkin et al. | 600/473 |
| 2010/0056928 A1 * | 3/2010 | Zuzak et al. | 600/476 |
| 2010/0104168 A1 * | 4/2010 | Dobbe | 382/134 |
| 2010/0160789 A1 * | 6/2010 | Dilworth | A61B 3/0025 600/476 |
| 2010/0292931 A1 * | 11/2010 | Wang | G01N 21/6408 702/19 |

FOREIGN PATENT DOCUMENTS

| | | |
|---|---|---|
| AU | 455496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/009727 | 5/1993 |
| WO | 94/020041 | 9/1994 |
| WO | 96/05873 | 2/1996 |

(56) References Cited

FOREIGN PATENT DOCUMENTS

| WO | 97/18007 | 5/1997 |
|---|---|---|
| WO | 99/13793 | 3/1999 |

OTHER PUBLICATIONS

Louis C. Argenta, MD and Michael J. Morykwas, PhD; "Vacuum-Assisted Closure: A New Method for Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

HYPERSPECTRAL IMAGING SYSTEMS AND RELATED METHODS

CROSS-REFERENCE TO RELATED APPLICATIONS

This application claims the priority of U.S. Provisional Patent Application Ser. No. 61/511,858 filed Jul. 26, 2011, the entire disclosure of which is specifically incorporated herein by reference.

BACKGROUND OF THE INVENTION

Field of the Invention

Embodiments of the invention relate to systems and methods for analyzing sublingual microcirculation perfusion and identifying particular nerve tracts.

Description of the Related Art

The ability to visualize and analyze spectra beyond the visible range provides a wide range of diagnostic opportunities. It is known that oxygenated tissue absorbs and reflects certain wavelengths of light (electromagnetic radiation will be referred to as "light" in this description) and is commercialized in pulse oximeters and $StO_2$ systems. For instance, one system analyzes seven specific wavelengths of light between approximately 600 and 800 nm to determine concentration of oxygen saturated hemoglobin, and concentrations of carboxyhemoglobin, methemoglobin, and hemoglobin. Previous hyperspectral imaging systems have used a liquid crystal tunable filter (LCTF), capable of only about one image every 30 seconds.

Existing systems can be used to visualize the sublingual vasculature in septic humans via orthogonal polarization spectral (OPS) imaging (see DeBacker et al., Am. J. Respir. Crit. Care Med., 2002, incorporated by reference herein) and via sidestream dark field (SDF) imaging (see Trzeciak et al., Intensive Care Med, 2008, incorporated by reference herein). However, such techniques can be difficult to use, since direct contact with the sublingual tissue is necessary, and even slight pressure on the tissue will alter the microcirculation. In addition, scoring the quality of the microcirculation is problematic. Several manual scoring means have been proposed (see Boerma et al, Crit. Care, 2005, incorporated by reference herein) but these are laborious and require a post-processing step.

OPS and SDF technologies have been available in a hand-held device for approximately a decade and numerous publications show the utility in detecting a tracking septic patients. However, routine bedside use has not been adopted in part due to the technical challenges of using the device and evaluating the output.

A non-contact imaging system that allows the evaluation of sublingual microcirculation perfusion rather than simply visualizing the vasculature would benefit the assessment and tracking of septic patients.

The ability to visualize and analyze spectra beyond the visible range may be used in other applications as well. For example, surgeons sometimes may have difficulty identifying specific areas of the anatomy during surgical procedures. A system capable of identifying nerve bundles or tracts would also be beneficial, for example, during such surgical procedures. Such a system could assist a surgeon in identifying which areas of the subject area were to be protected and which areas required surgical procedures.

SUMMARY OF THE INVENTION

From the foregoing discussion, it should be apparent that a need exists for a system and method for analyzing sublingual microcirculation perfusion and for anatomical identification, including nerve tracts.

The method in the disclosed embodiments substantially includes the steps necessary to carry out the functions presented above with respect to the operation of the described system.

Exemplary embodiments incorporate a digital micro-mirror device (DMD) to dynamically reflect light to a subject area. In certain embodiments, broadband light is diffracted through a slit, reflected from a grid of digitally-controlled programmable micro-mirrors, and optically directed to a digital camera through a liquid light guide (LLG), similar to an optical fiber that has an increased capacity for transmitting light. Particular embodiments illuminate tissue with reflected light and analyze response light for wavelengths in the infrared and near infrared ranges simultaneously, generating an entire spectral signature.

Certain embodiments control the state of each mirror individually to illuminate a subject area with a programmed selection of wavelengths of light. An optical detector (e.g. a camera) can measure the reflection or fluorescence of the response spectrum. The programmed spectrum may simply be a single bandpass—similar to the LCTF output—or a more complex combination of wavelengths that cannot be duplicated by the LCTF. Since the DMD hyperspectral imager uses mirrors instead of liquid crystals, the tuning time can be faster and the wavelength range broader. Using a micromirror array and DLP technology lets the user program the source illumination using predetermined complex spectra or color mixtures of light.

Certain embodiments may comprise a system for analyzing sublingual microcirculation perfusion. In particular embodiments, the system may comprise: a light source; a digital micro-mirror device; an optical detector; an analyzer; and a controller coupled to the digital micro-mirror device. In specific embodiments, the light source may be configured to emit light to the digital micro-mirror device, and the digital micro-mirror device may be configured to direct a reflected light to a subject area. In certain embodiments, the controller may be configured to alter a parameter of the reflected light, and the optical detector may be configured to detect a response light from the subject area. In particular embodiments, the analyzer may be configured to analyze the response light and calculate an index indicative of the sublingual microcirculation perfusion of the subject area.

In specific embodiments, the index may comprise calculations of $pCO_2$ or $pO_2$ levels of tissue in the subject area. In certain embodiments, the controller may be configured to alter the wavelength of the reflected light directed to the subject area. In certain embodiments, the controller may be configured to alter the location of the reflected light directed to the subject area. Particular embodiments may comprise a filter configured to generate a spectrum of light from the light source. In certain embodiments, the controller is configured to alter the parameter of the reflected light at least once per second. In specific embodiments, the controller may be configured to alter the parameter of the reflected light at least twice per second. In particular embodiments, the controller may be configured to alter the parameter of the reflected light at least three times per second and the index may be calculated with a fuzzy inference system or with time series analysis methods.

In certain embodiments, the analyzer may be configured to generate an image of the subject area wherein the level of sublingual microcirculation perfusion is indicated by color. In particular embodiments, the analyzer may comprise a computer-readable medium configured to analyze the response light and calculate an index indicative of the sublingual microcirculation perfusion of the subject area. In certain embodiments, the analyzer may be configured to alert a user when the sublingual microcirculation perfusion is outside of a defined range. In specific embodiments, the analyzer may be configured to alert a user when the sublingual microcirculation perfusion indicates the subject area has developed systemic inflammatory response syndrome.

Particular embodiments may comprise a system for identifying a nerve tract, where the system comprises a light source; a digital micro-mirror device; an optical detector; an analyzer; a controller coupled to the digital micro-mirror device; and a stimulator configured to provide a stimulus to a nerve tract. In certain embodiments, the light source may be configured to emit light to the digital micro-mirror device. In particular embodiments, the digital micro-mirror device may be configured to direct a reflected light to a subject area. In certain embodiments, the controller may be configured to alter a parameter of the reflected light. In specific embodiments, the optical detector may be configured to detect a response light from the subject area. In certain embodiments, the analyzer may be configured to analyze the response light and generate an image of the subject area wherein the nerve tract is distinguished from an area surrounding the nerve tract.

In particular embodiments, the analyzer may be configured to generate an image of the subject area wherein the nerve tract is a different color than the area surrounding the nerve tract. In certain embodiments, the stimulator may be configured as a flashing light. In particular embodiments, the stimulator may be a component of eyewear configured to be worn by a subject. In specific embodiments, the controller may be configured to alter the parameter of the reflected light at least once per second. In particular embodiments, the controller may be configured to alter the parameter of the reflected light at least twice per second. In certain embodiments, the controller may be configured to alter the parameter of the reflected light at least three times per second. In specific embodiments, the analyzer may comprise a computer-readable medium configured to analyze the response light and generate an image of the subject area.

Particular embodiments may also comprise a method for analyzing sublingual microcirculation perfusion, where the method comprises: directing light to a digital micro-mirror device; directing a reflected light from the digital micro-mirror device to a subject area; dynamically controlling the reflected light from micro-mirror device to the subject area; detecting a response light from the subject area; and analyzing the response light from the subject area and calculating an index indicative of the sublingual microcirculation perfusion of the subject area.

In certain embodiments, dynamically controlling the reflected light from the micro-mirror device to the subject area may comprise altering a parameter of the reflected light at least once or twice per second. In specific embodiments, dynamically controlling the reflected light from the micro-mirror device to the subject area may comprise altering a parameter of the reflected light at least three times per second. In particular embodiments, the parameter may comprises the wavelength or the location of the reflected light.

Particular embodiments may comprise a method for identifying a nerve tract, the where method comprises: providing a stimulus to a nerve tract; directing light to a digital micro-mirror device; directing a reflected light from the digital micro-mirror device to a subject area; dynamically controlling the reflected light from micro-mirror device to the subject area; detecting a response light from the subject area; and analyzing the response light from the subject area and generating an image of the subject area, where the nerve tract is distinguished from an area surrounding the nerve tract.

In certain embodiments, dynamically controlling the reflected light from the micro-mirror device to the subject area may comprise altering a parameter of the reflected light at least once per second.

In particular embodiments, dynamically controlling the reflected light from the micro-mirror device to the subject area may comprise altering a parameter of the reflected light at least twice per second. In certain embodiments, dynamically controlling the reflected light from the micro-mirror device to the subject area may comprise altering a parameter of the reflected light at least three times per second. In certain embodiments, the parameter comprises the wavelength or the location of the reflected light.

Other features and associated advantages will become apparent with reference to the following detailed description of specific embodiments in connection with the accompanying drawings.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

BRIEF DESCRIPTION OF THE DRAWINGS

The following drawings form part of the present specification and are included to further demonstrate certain aspects of exemplary embodiments of the present invention.

DETAILED DESCRIPTION OF EXEMPLARY EMBODIMENTS

Various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

In the following description, numerous specific details are provided, such as examples of material selections, dimensions, etc., to provide a thorough understanding of the present embodiments. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
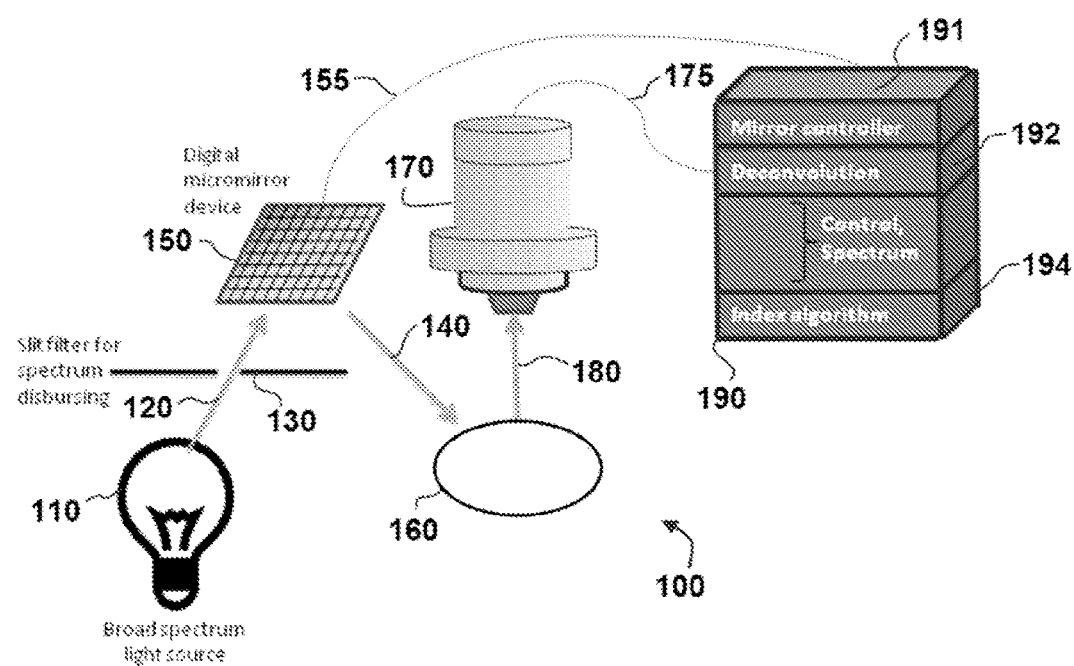
FIG. 1 is a schematic diagram illustrating a system according to a first exemplary embodiment.

FIG. 1 illustrates one embodiment of a system 100 for conducting hyperspectral imaging. In this exemplary embodiment, system 100 comprises a light source 110, a filter 130, a digital micromirror device (DMD) 150, optical detector 170 and controller 190. In the exemplary embodiment shown, DMD 150 can be provided by Texas Instruments® DLP division. In this embodiment, DMD 150 is coupled to controller 190 via electrical coupling 155, and detector 170 is coupled to controller via electrical coupling 175. Electrical couplings 155 and 175 may comprise wireless or wired couplings, including fiber optic couplings.

A general overview of the operation of system 100 will be presented initially, followed by a more detailed description of specific embodiments. During operation, system 100 can be used to identify or analyze certain conditions or components based on the light reflected or fluoresced from (or absorbed by) the subject. For example, light source 110 can direct light 120 through filter 130 to DMD 150, which is controlled by controller 190 to direct reflected light 140 to a subject area 160. As used herein, the term "light" will be used to refer to electromagnetic radiation. Response light 180 is reflected and/or fluoresced from subject area 160 and is detected by optical detector 170, which communicates to an analyzer 192 data relating to response light 180. This data can then be deconvolved relative to the direct reflected light 140 to analyze subject area 160.

In specific embodiments, controller 190 comprises several individual components including, for example, a mirror controller 191 to control DMD 150. Controller 190 may also comprise analyzer 192 to deconvolve or analyze the data received from optical detector 170. In certain embodiments, controller 190 may used to control DMD 150 so that DMD 150 directs reflected light 140 to provide a dynamic stimulus to subject area 160. In particular embodiments, parameters of reflected light 140, including for example, frequency, intensity, and location, can be altered in rapid succession (e.g., multiple times per second) and the response from subject area 160 can be analyzed via changes in response light 180. In this manner, multiple variables can be determined in sub-second periods permitting their analysis in a real-time algorithm. Such real-time algorithms may be executed in an index algorithm 194 to consolidate these multiple variables into an index of fewer dimensions. Particular embodiments illuminate tissue with reflected light and analyze response light for wavelengths between 380 and 1600 nm simultaneously, generating an entire spectral signature.

In specific embodiments, system 100 may be used to detect changes in mucosal microcirculatory perfusion, including for example, conditions associated with sepsis. In the circulatory shock and inflammation associated with sepsis, microcirculation is disturbed secondary to coagulation leading to microvascular thrombosis, adhesion of leukocytes to the vasculature, and the decreased deformability of red blood cells (RBCs). These factors can lead to microcirculatory shunting, cellular distress, and organ failure.

Previous hyperspectral imaging systems have used a liquid crystal tunable filter (LCTF), capable of only about one image every 30 seconds. However, exemplary embodiments of system 100 are capable of generating images every 300 ms. Although specific exemplary embodiments will be described in detail, it is understood that variations may be implemented in other exemplary embodiments of the present disclosure.

In one exemplary embodiment, light source 110 directs broadband light 120 that is diffracted through a slit filter 130. The light passing through slit filter 130 is reflected from DMD 150, and optically directed to subject area 160. By individually controlling the state of each mirror of DMD 150, the subject area 160 is illuminated with a programmed selection of wavelengths of reflected light 140. Optical detector 170 can then measure the spectrum of response light 180 reflected from subject area 160. The programmed spectrum of light 140 may simply be a single bandpass—similar to the liquid crystal tunable filer (LCTF) output—or a more complex combination of wavelengths that cannot be duplicated by the LCTF, including for example, ultraviolet (UV) through near-infrared (NIR).

The use of mirrors incorporated into DMD 150, rather than liquid crystals allows reflected light 140 to be manipulated faster and over a broader wavelength range. System 100 further allows a user to program controller 190 to provide a predetermined complex spectra or color mixtures of reflected light 140 reflected from DMD 150.

Numerous changes occur in the sublingual microvasculature during medical conditions, including for example, systemic inflammatory response syndrome (SIRS) or sepsis. Of these, several factors can be assessed by the system 100. For example, decreases in perfusion will result in poorer oxygenation of the tissue, poorer $CO_2$ clearance, and local acidosis. As a result of disseminated intravascular coagulation (DIC), a potential step in the sequence of SIRS or sepsis, fibrin can form in the microvasculature. The presence of fibrin indicates a pathologic condition. Further, red blood cells (RBCs) can become static or sluggish since they are not able to deform to the diameter of the capillary and the available capillary diameter decreases with the thrombin formation.

Tissue $pCO_2$ levels can be detected by variable absorption of near infrared (NIR) wavelengths of reflected light 140. Oxyhemoglobin can be detected with variable absorption of red and NIR wavelengths of reflected light 140. When exposed to reflected light 140, fibrin will fluoresce at certain frequencies, which can also be detected by optical detector 170.

In this embodiment, system 100 images each of these attributes in succession by varying the illuminating spectra of reflected light 140 for each factor. In certain embodiments, system 100 can then collect the reflected or fluoresced response light 180 and analyzer 192 can calculate variables including $pO_2$, $pCO_2$, and fibrin content, combining them into an index algorithm 194 calculated by software incorporated in controller 190. This index can be trended to track the progression of sepsis, for example. A fuzzy inference system (FIS) is one means of generating such an algorithm. Using weighting factors, time sequence relationships, and relative changes in values, an index is determinable. A decrease in $pO_2$ followed by an increase in $pCO_2$ in the presence of fibrin would constitute an exemplary embodiment.

Figure 2:
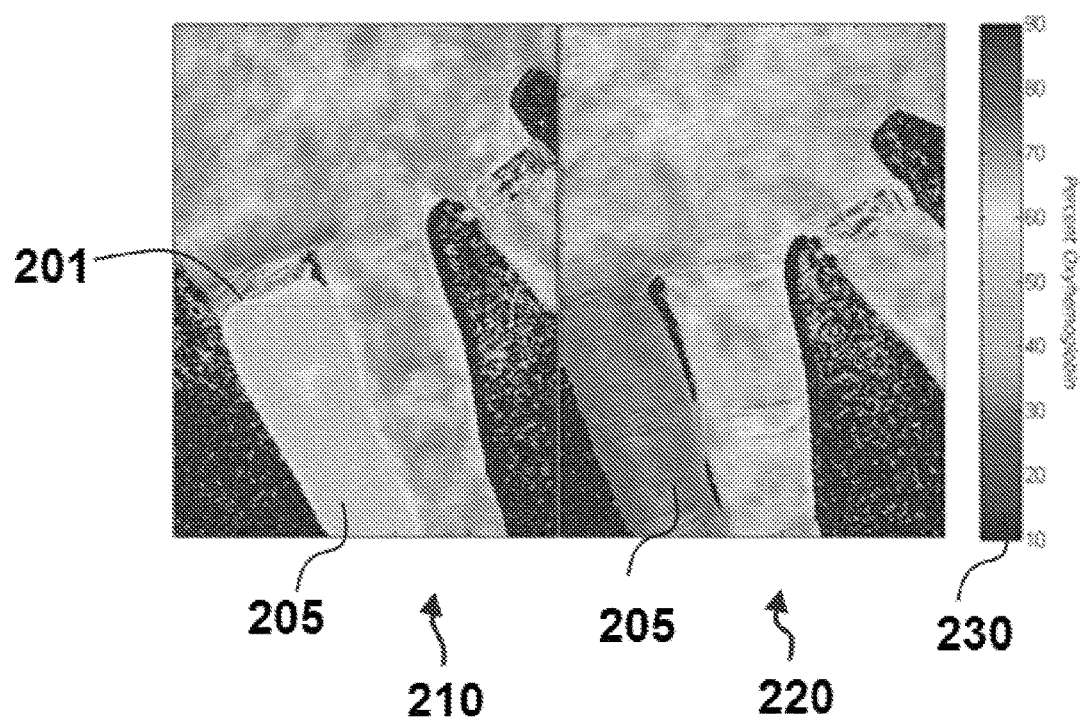
FIG. 2 is an image generated by the embodiment according to FIG. 1.

As shown in FIG. 2, system 100 can be used to display a visual image of changes in sublingual microcirculation perfusion. In image 210 to the left generated by system 100, a rubber band 201 has been placed around far left digit 205 to constrict blood flow. As indicated in graph 230 on the right, the percent of oxyhemoglobin is measured at approximately 50 percent (based on the color of digit 205). In image 220 to the right generated by system 100, the constriction has been removed and the blood flow to the digit increased. As indicated by graph 230, the percent of oxyhemoglobin has increased to approximately 80 percent due to the hyperfusion following the release of pressure. While visible light will eventually indicate a paling of the skin when blood flow is restricted, system 100 can indicate changes in blood flow much sooner and with greater sensitivity than would be visible with exposure of the skin to visible light. The image shown in FIG. 2 is merely one example of the type system 100 is capable of generating. Other images, for example, may comprise an index that includes the $pO_2$, $pCO_2$, and fibrin content, as previously discussed.

In another exemplary embodiment, system 100 can be used to detect relatively static RBCs in the sublingual microcirculation to provide an indication of DIC and progressing sepsis. In this embodiment, providing an excitation spectrum of reflected light 140 near 400 nm will cause RBCs to fluoresce response light 180. With the high frame rate available with system 100, sequential images captured by optical detector 170 can be compared to estimate the velocity of the RBCs. Under normal conditions, capillary blood velocity is approximately 900 µm/sec. With a relatively even distribution of RBCs in the plasma, a frame rate of 300 ms will give the appearance of threads of RBCs within the vasculature. In pathophysiologic conditions, portions of the capillary have essentially zero flow resulting in isolated clumps of RBCs, which would be clearly distinguishable from the thread-like appearance of normal movement.

As described herein, system 100 provides a non-contacting means of assessing sublingual perfusion and DIC, which can overcome one important shortcoming of the existing OPS and SDF technologies. Further, this will allow straightforward calculations in near real-time of $pO_2$, $pCO_2$, and fibrin content rather than post-processing assessment of, for instance, capillary density by counting the vessels crossing arbitrary lines in a field of view. Furthermore, reliance on a combination of variables that are present in the condition is more reliable than a univariate system. System 100 can generate multiple measurements by altering the illuminating spectrum on successive sweeps of the field of view.

In certain embodiments, system can also provide a visual display of subject area 160 encoded with the physiologic information, in addition to providing a summary calculation. While the index is calculated and displayed, each element of the index can also be available for quality assurance and user acceptance.

In another exemplary embodiment, system 100 can be configured to identify specific anatomical features, including for example, nerve bundles or tracts. For example, in a specific embodiment, system 100 can be configured to identify primary optic or cochlear nerve tracts that are myelinated. The general principles of operation in this embodiment are similar to those of the previously described embodiment used for the detection of SIRS or sepsis. For example, light source 160 directs light 120 through filter 130 to DMD 150, which is controlled by controller 190. DMD 150 directs reflected light 140 to subject area 160, which reflects and/or fluoresces response light 180 that is detected by optical detector 170. The light detected by optical detector 170 can then be analyzed by controller 190 (e.g. via specific software incorporated in controller 190) to identify specific nerve tracts.

Figure 3:
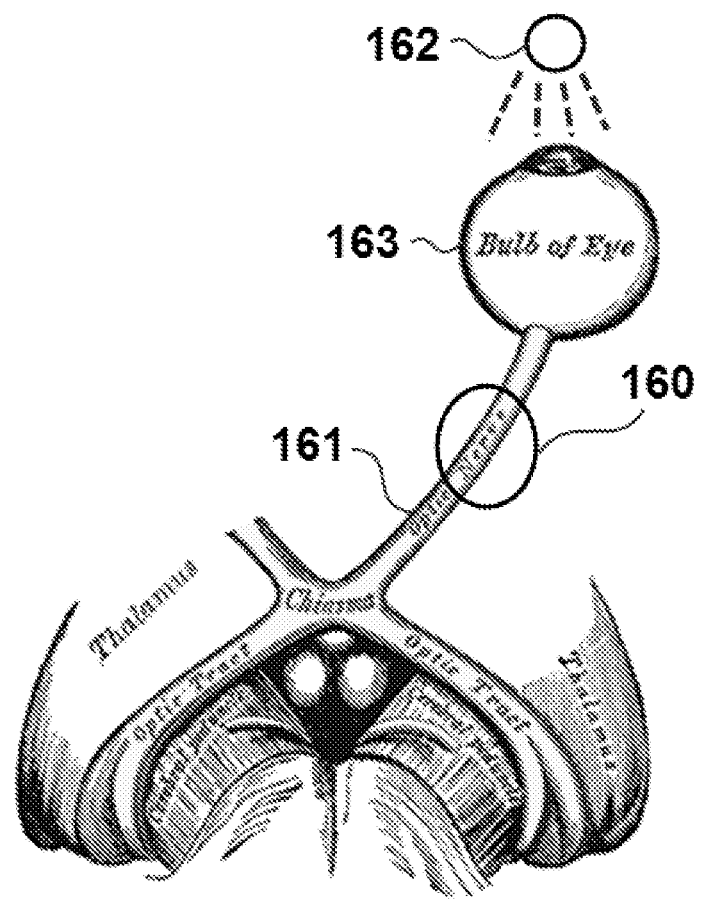
FIG. 3 is a diagram of an anatomical area analyzed by the embodiment according to FIG. 1.

As shown in FIG. 3, in one specific embodiment subject area 160 may be an area approximately 3 $cm^2$ comprising an optic tract 161 with a length of approximately 30 mm (orbital portion) and a 3 mm diameter. Each nerve bundle contains about 1.2 million individual nerve fibers, providing sufficient volume for an adequate signal to noise ratio, as described further below.

In certain embodiments, during operation of system 100 action potentials can be generated on optic tract 161 by a periodic and repetitive stimulation provided by a stimulator 162. For example, optic tract 161 can be excited by applying stimulator 162, which may be configured as a flashing light incorporated into a goggle in certain embodiments. Exposure to such stimulation to receptors (e.g. the bulb of the eye 163) coupled to optic tract 161 can generate a response signal in optic tract 161, even if the subject is under anesthesia, as explained more fully below.

Under resting conditions, sodium pumps on the lipid bilayer of optic tract 161 actively move $Na^+$ ions to the outside of optic tract 161 resulting in a resting potential of about −70 mV (inside relative to outside). During an action potential, voltage sensitive sodium channels are triggered to open in response to a stimulus. This can allow $Na^+$ ions to migrate to the inside of the membrane in response to the concentration gradient. A refractory period then prohibits the stimulus from reactivating that segment, keeping the electrical "signal" moving unidirectionally on optic tract 161. This refractory period is also a result of a change in the protein configuration of the sodium channel.

With constant stimulation of optic tract 161 by stimulator 162, there will be at any given time a constant flux of open, closed, and refractory ion channels on optic tract 161 relative to other nerve tracts (e.g., cochlear given a lack of auditory stimulation). The signature of this mixture of open, closed, and refractory channels is identified by the appropriate spectral signature made possible by system 100. This can allow a user to differentiate the primary nerve bundles such as optic tract 161 from other nerve tracts.

Figure 4:
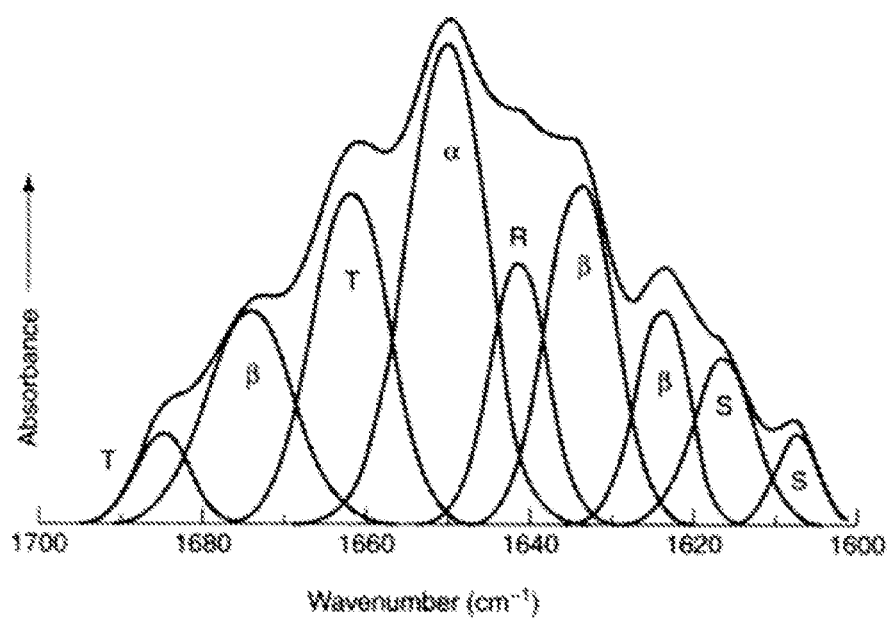
FIG. 4 is a spectrum of response light generated by the embodiment according to FIG.

A spectrum of response light 180 indicative of the myelin layer can be found by targeting both the lipids (e.g., glycolipid) and proteins (e.g., myelin basic protein) of the layer. One example of a spectrum of myelin basic protein is shown in FIG. 4. Protein conformation and subsequent quantification is known to be possible with UV-visible spectroscopy. Further enhancement of the signal to noise ratio may also be achieved by a principle component analysis of the spectrum signatures. While a single nerve fiber would not provide an adequately target size to analyze, the optic nerve bundle comprises over one million nerve fibers, greatly increasing the concentration of target proteins.

Figure 5:
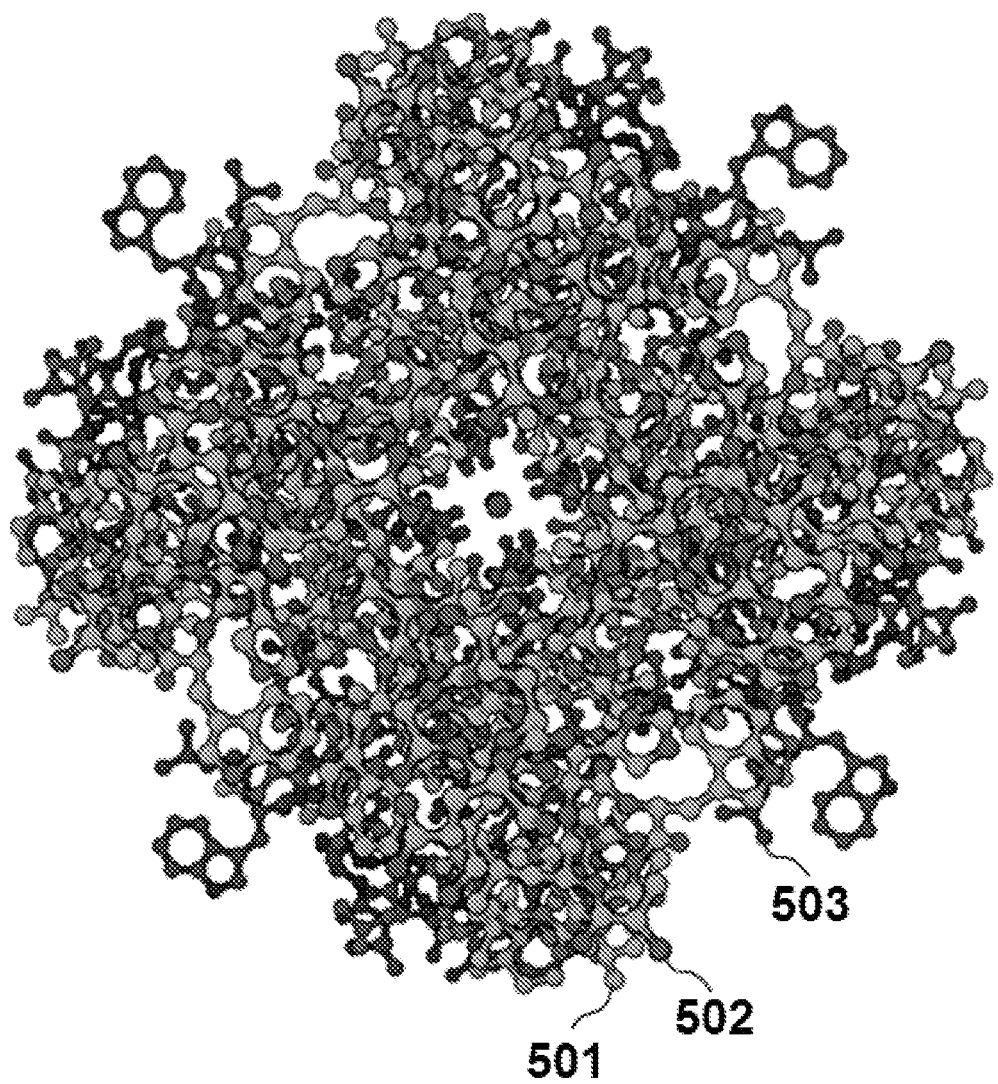
FIG. 5 is an image of nerve bundles generated by the embodiment according to FIG. 1.
Figure 6:
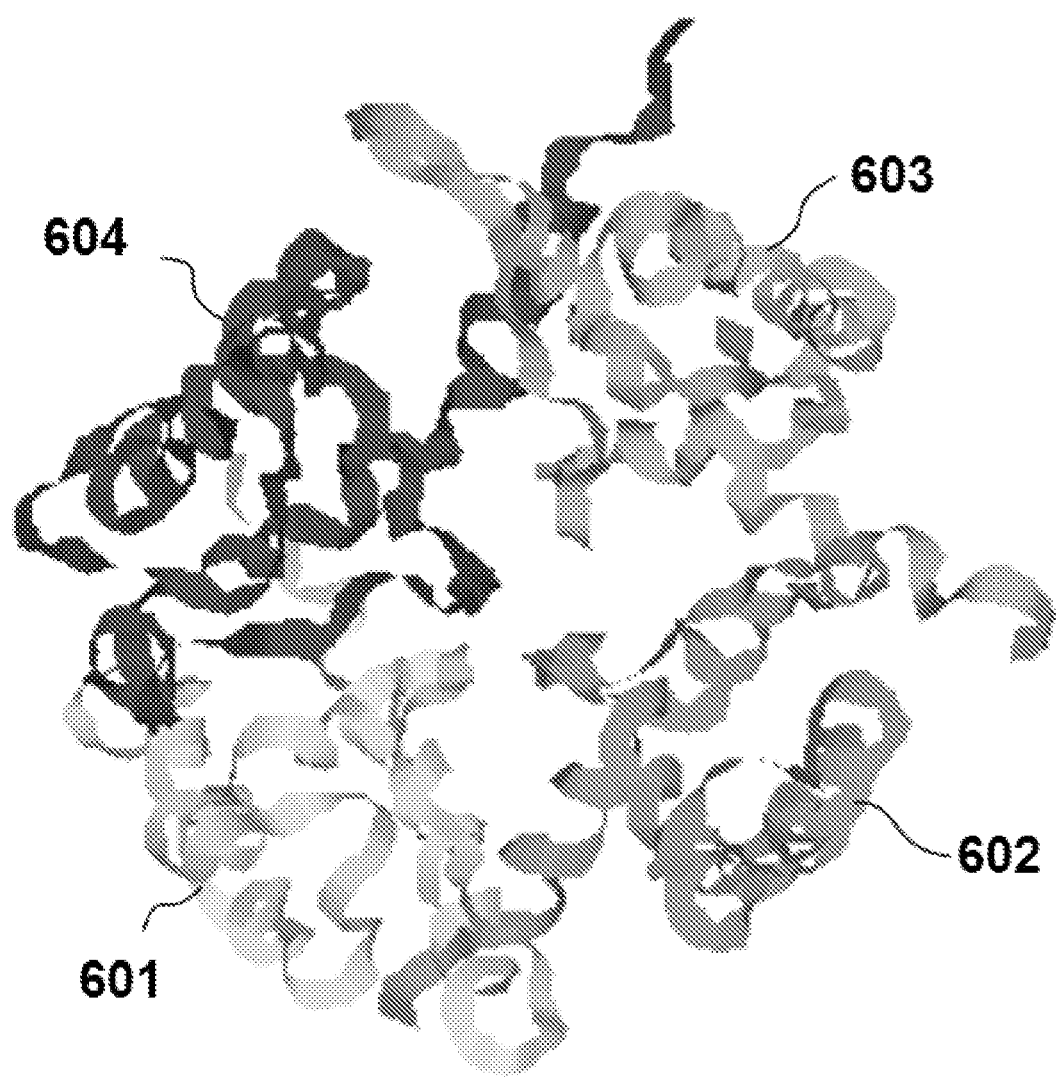
FIG. 6 is an image of ion channels generated by the embodiment according to FIG. 1.

In certain embodiments, system 100 can generate a two dimensional image with the concentration of the target encoded on the physical image. The oxygenation of various digits is shown by way of example of this technique. The targeted nerve bundles are similarly encoded on a 2D image intraoperatively as shown in FIG. 5. The varying oxygenation levels can be indicated by different colors 501, 502 and 503 shown in FIG. 5. Models of ion channels are also shown in FIG. 6 and differentiated by colors 601, 602, 603, and 604.

Certain embodiments may also incorporate an injection of a material that would selectively bind to myelin. This could allow the myelin to be more readily detectable with spectroscopy. In addition, this technique may be useful for evaluating degeneration of myelin sheaths, as is the case with various neurological disorders such as multiple sclerosis, Guillain-Barre syndrome, and Charcot-Marie-Tooth disease. Hyperspectral imaging incorporated by system 100 may also be used for establishing a baseline intensity of myelin presence and allow for tracking of degenerating myelin either during progression of the disease or as an indicator of pending neuropathy.

The following references are incorporated by reference herein:
U.S. Pat. No. 6,640,130
U.S. Pat. No. 6,770,484
U.S. Pat. No. 6,937,885
U.S. Patent Publication 2010/0056928
"Detection and Analysis of the Intestinal Ischemia Using Visible and Invisible Hyperspectral Imaging", IEEE Transactions on Biomedical Engineering, Vol. 58, No. 8, August 2010.
"Imaging Hemoglobin Oxygen Saturation in Sickle Cell Disease Patients Using Noninvasive Visible Reflectance Hyperspectral Techniques: Effects of Nitric Oxide", Am J Physiol Heart Circ Physiol 285:H1183-9, 2003.

I claim:

1. A method for analyzing microcirculation perfusion of tissue to detect conditions associated with sepsis without contacting a subject area, the method comprising:
   directing light to a digital micro-mirror device configured to reflect the light for illuminating a subject area of the tissue;
   directing a reflected light from the digital micro-mirror device to illuminate the subject area without contacting the tissue;
   dynamically controlling the reflected light from the micro-mirror device to the subject area, wherein a wavelength and a location of the reflected light impinging on the subject area is altered;
   detecting a response light reflected from the subject area without contacting the subject area and providing response data related to the response light;
   deconvolving the response data relative to the reflected light and providing deconvolved data;
   calculating variables including $pO_2$ levels, $pCO_2$ levels, and fibrin content of the subject area based on the deconvolved data;
   generating an index value, based on the variables for the $pO_2$ levels, $pCO_2$ levels, and fibrin content, indicative of changes in a microcirculation perfusion of the subject area for detecting conditions associated with sepsis, wherein the index value is generated using a fuzzy inference system; and
   displaying on a display an image of the subject area showing the index value indicative of a change in the microcirculation perfusion of the subject area.

2. The method of claim 1 wherein dynamically controlling the reflected light from the micro-mirror device to the subject area comprises altering the wavelength and the location of the reflected light at least once per second.

3. The method of claim 1 wherein dynamically controlling the reflected light from the micro-mirror device to the subject area comprises altering the wavelength and the location of the reflected light at least twice per second.

4. The method of claim 1 wherein dynamically controlling the reflected light from the micro-mirror device to the subject area comprises altering the wavelength and the location of the reflected light at least three times per second.

5. The method of claim 1 wherein displaying the image of the subject area includes indicating the change in the microcirculation perfusion of the subject area by a different color.

6. The method of claim 1, further comprising alerting a user when the change in the microcirculation perfusion of the subject area is outside of a defined range.

7. The method of claim 1, further comprising alerting a user when the microcirculation perfusion of the subject area indicates the subject area has developed systemic inflammatory response syndrome.

* * * * *